United States Patent [19]

Yokoyama et al.

[11] 4,279,165
[45] Jul. 21, 1981

[54] APPARATUS FOR MEASURING COHESION FORCE OF PARTICULATE MATERIALS

[75] Inventors: Tohei Yokoyama; Shintaro Asakura, both of Kyoto; Kiyoshi Urayama, Yahata; Kenji Fujii, Kyoto, all of Japan

[73] Assignee: Kabushiki Kaisha Hosokawa Funtai Kogaku Kenkyusho, Osaka, Japan

[21] Appl. No.: 93,774

[22] Filed: Nov. 13, 1979

[30] Foreign Application Priority Data

Aug. 9, 1979 [JP] Japan .................................. 54/101656

[51] Int. Cl.³ .............................................. G01N 3/08
[52] U.S. Cl. .................................................. 73/826
[58] Field of Search ................. 73/826, 827, 834, 835, 73/837, 842, 845

[56] References Cited

U.S. PATENT DOCUMENTS 3,057,182  10/1962  Hackett ............................. 73/834 X

FOREIGN PATENT DOCUMENTS 620869  11/1978  U.S.S.R. .................................... 73/845

Primary Examiner—Jerry W. Myracle
Attorney, Agent, or Firm—Edwin E. Greigg

[57] ABSTRACT

An apparatus for measuring the cohesion force of a particulate material. The apparatus comprises a bottomed container composed of a fixed container segment and a movable container segment for containing the particulate material, a driving device for moving the movable container segment perpendicularly to the plane of separation of the container to divide the particulate material in the container into two, and a unit for detecting the external force to be applied to the movable container segment by the driving device. At least the movable container segment is suspended from and retained by swingable or deflectable support members.

6 Claims, 9 Drawing Figures

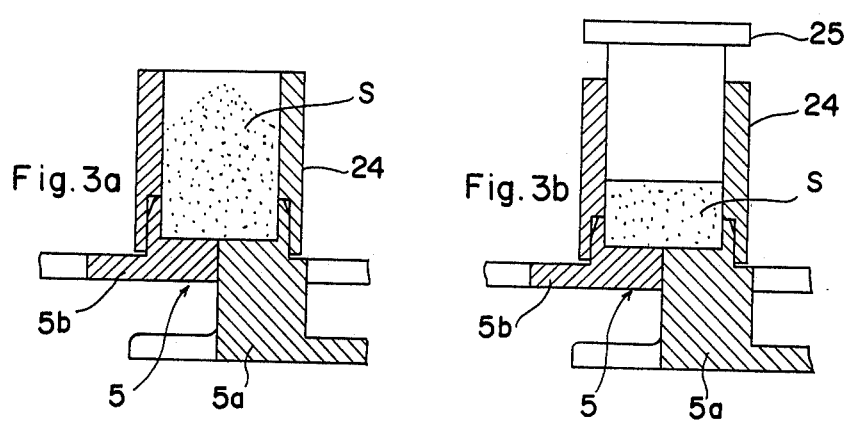
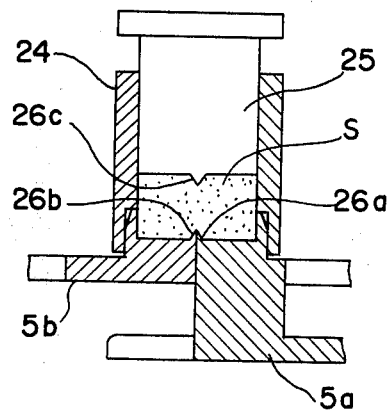
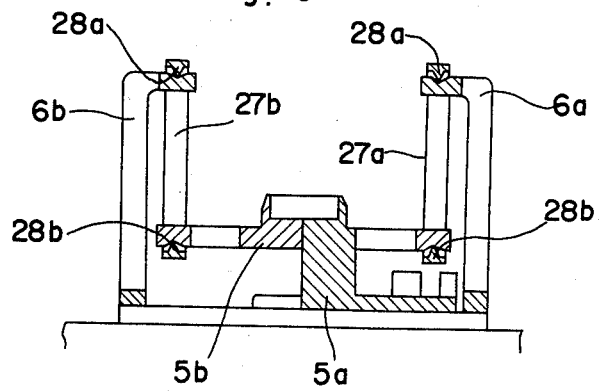

APPARATUS FOR MEASURING COHESION FORCE OF PARTICULATE MATERIALS

BACKGROUND OF THE INVENTION

The present invention relates to improvements in an apparatus for measuring the cohesion force of particulate materials.

Various apparatus are known for measuring the cohesion force of particulate materials. They include an apparatus comprising a bottomed container composed of a fixed container segment and a movable container segment separable from each other for containing the particulate material as compactly placed therein, a drive assembly for moving the movable container segment in a direction approximately perpendicular to the plane of separation of the container to divide the particulate material in the container into two, and an external force detecting unit for detecting the external force to be applied to the movable container segment by the drive assembly. With this apparatus, the container segments are pulled away from each other by the drive assembly, with the bottomed container filled with a specimen of particulate material as compacted therein, and at this time, the external force detecting unit measures the tensile strength of the particulate material. The cohesion force of the material is determined based on the measurement. The invention relates to improvements in the apparatus of this type.

FIG. 8 shows such an apparatus heretofore available. The apparatus includes a bottomed container 5' comprising a fixed container segment 5a' and a movable container segment 5b' which is movably supported on ball bearings 33. Since the ball bearings 33 are thus used, the conventional apparatus requires extremely high precision in machining the rolling surface or groove for the bearings 33. Moreover, even if fabricated with high precision, the apparatus has another drawback that the ball bearings 33 involve unnegligible rolling friction which impairs the accuracy of measurements despite the resulting increase in the overall cost of the apparatus. The apparatus has still another drawback. When the container 5' is filled with a specimen of particulate material, S, the specimen must be compacted under a load, but there is a limitation on the load applicable to the specimen S in view of the strength of the rolling surface for the ball bearings 33. This in turn imposes limitations on the measuring condition and, accordingly, on the usefulness of the apparatus.

SUMMARY OF THE INVENTION

The present invention, accomplished to overcome the foregoing drawbacks of the conventional apparatus, provides an apparatus characterized in that at least the movable container segment of the two segments constituting a bottomed container is suspended from and retained by support means which is swingable or deflectable.

Since the movable container segment is thus retainable in suspension, there is no need to use ball bearings that would require a precision-finish rolling surface, nor is it necessary to consider any rolling friction. The apparatus can therefore be manufactured at a relatively low cost with high precision. Because the particulate specimen can be compacted with application of considerably great load, the apparatus is usable for a wider variety of particulate materials and settable for widely varying measuring conditions and has a greatly increased range of applications to the measurement of properties of various particulate materials.

Other objects and advantages of the invention will be apparent from the following description.

BRIEF DESCRIPTION OF THE DRAWINGS

FIGS. 3(a) and 3(b) are fragmentary views in vertical section showing a specimen filling procedure;

FIGS. 4 to 6 are fragmentary views in vertical section showing other embodiments;

DESCRIPTION OF THE PREFERRED EMBODIMENTS

Figure 1:
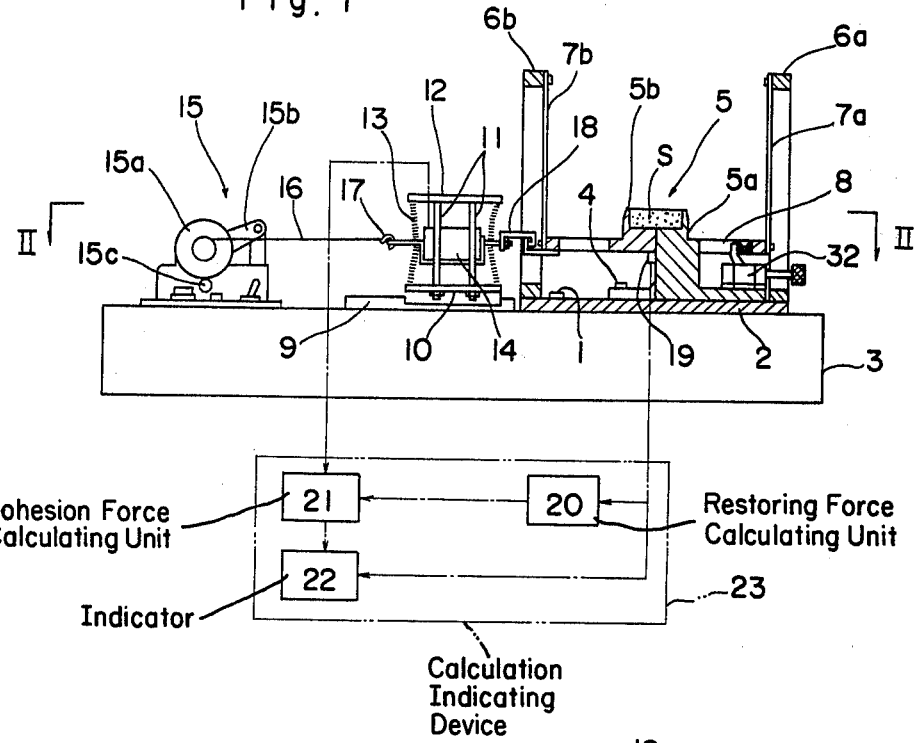
FIG. 1 is a side elevation partly broken away and showing an apparatus of this invention for measuring the cohesion force of particulate materials.
Figure 2:
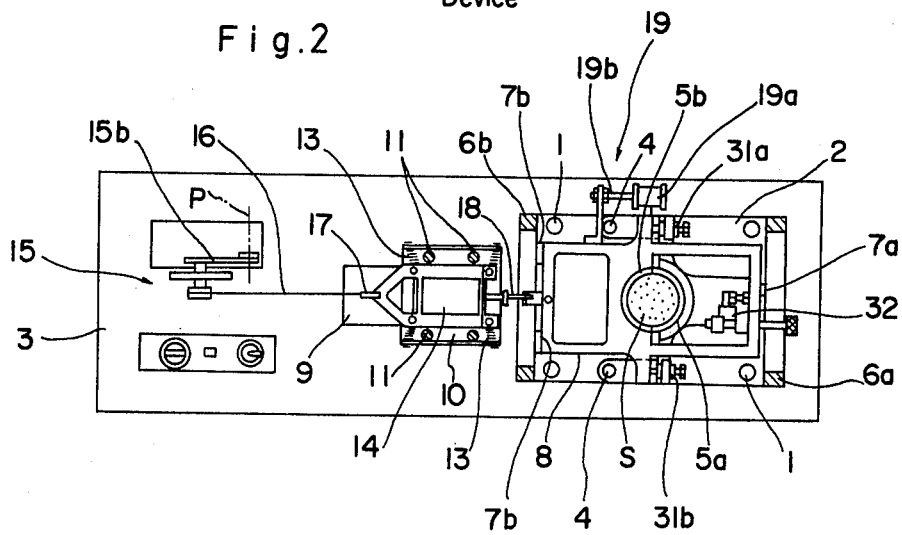
FIG. 2 is a view showing the apparatus as it is seen in the direction of the line II—II in FIG. 1.

With reference to FIGS. 1 and 2, a support frame 2 having position adjusting bolts 1 at its four corners is placed on a base 3 which is provided with upright positioning pins 4 fitting in the support frame 2. A bottomed container 5 for containing a specimen of particulate material, S, as compactly filled therein comprises a fixed container segment 5a secured to the support frame 2 and a movable container segment 5b. Front and rear plate springs 7a, 7b depend respectively from a pair of gate-shaped posts 6a, 6b extending upright from the support frame 2. The movable container segment 5b is attached to a movable support 8 which is attached to the lower ends of the plate springs 7a, 7b.

A lower plate 10 slidably mounted on a guide 9 on the base 3 has at its four corners posts 11 by which an upper plate 12 is attached to the lower plate 10. Four tension coil springs 13 extending between and attached to the plates 10 and 12 support a detecting unit 14 in suspension. The unit 14 utilizes a strain gauge.

A wire 16 paid off from an electric winch 15 mounted on the base 3 is provided at its leading end with a hook 17 attached to one end of the detecting unit 14, the other end of which is connected by a hook 18 to the movable support 8, such that the lower plate 10 and the detecting unit 14 thereon are movable by the winch 15 to move the movable support 8 while deflecting the plate springs 7a, 7b. Consequently the movable container segment 5b is movable away from the fixed container segment 5a in a horizontal direction substantially perpendicular to the plane of separation of the container 5.

The winch 15 comprises a take-up wheel 15a and an arm 15b supporting the wheel 15a and turnable about an axis P. With the turn of the arm 15b, the take-up wheel 15a is brought into or out of contact with a drive wheel 15c. With the wheel 15a in contact with the wheel 15c, the tension of the wire 16 gives the wheels 15a, 15c increased contact pressure which assures frictional power transmission from the wheel 15c to the wheel 15a.

The movable support 8 can be locked by the cooperation of stoppers 31a, 31b and holder 32 to ensure the assembly of the bottomed container 5.

An electromagnetic coil 19a fixed to the support frame 2 and a movable iron core 19b connected to the movable support 8 provide a differential transformer 19.

The detecting unit 14 and the differential transformer 19 are coupled to a calculation indicating device 23 including a restoring force calculating unit 20, a cohesion force calculating unit 21 and an indicator 22.

Based on the information from the differential transformer 19, the restoring force calculating unit 20 is adapted to calculate the sum of the gravitational restoring force resulting from the displacement of the movable support 8 and the movable container segment 5b from their spontaneously resting position and the elastic restoring force of the plate springs 7a, 7b due to their deflection. Based on the information from the detecting unit 14 and the restoring force calculating unit 20, the cohesion force calculating unit 21 calculates the cohesion force of the specimen S in the container 5 by subtracting the sum of the restoring forces from the external force applied to the specimen S to divide the specimen S.

By a meter, record or some other suitable means, the indicator 22 indicates the detected cohesion force based on the information from the cohesion force calculating unit 21 and the distance of displacement of the movable container segment 5b based on the information from the differential transformer 19.

To compactly fill the container 5 with the specimen S, a cylinder 24 is fittable around the segments 5a, 5b as fitted to each other to form the container 5 as seen in FIG. 3(a), and a weight 25 is fittable into the cylinder 24 to compact the specimen S therein as shown in FIG. 3(b).

The apparatus will be used in the following manner. As illustrated in FIGS. 3(a) and 3(b), a specimen S is placed into the container segments 5a, 5b in a suitably compacted state by the use of the cylinder 24 and the weight 25. The cylinder 24 and the weight 25 are thereafter removed from the container 5. Depending on the kind of the specimen S or on the measuring condition, the portion of the specimen S above the upper end of the container 5 may be scraped off to complete the specimen filling procedure. The winch 15 then applies an external force to the movable container segment 5b. The external force is delivered through the wire 16, hook 17, detecting unit 14 and hook 18 to the movable support 8. This force acts to pull the movable container segment 5b away from the fixed container segment 5a and to divide the specimen S in the bottomed container 5 at the plane of separation thereof. Consequently the mass of the specimen S is broken into two. At this time, based on the information from the differential transformer 19, the restoring force calculating unit 20 calculates the sum of the gravitational restoring force resulting from the displacement of the movable support 8 and the movable container segment 5b and the elastic restoring force of the plate springs 7a, 7b due to their deflection. On the other hand, based on the information from the detecting unit 14 and the restoring force calculating unit 20, the cohesion force calculating unit 21 calculates the cohesion force of the specimen S in the container 5 by substracting the sum of the restoring forces from the external force applied to the specimen S to divide the same. The result is indicated on the indicator 22. Since the container segment 5b is movably retained in suspension by the plate springs 7a, 7b in place of the ball bearings 33 conventionally used, the cohesion force can be measured with high accuracy free of the foregoing drawbacks heretofore experienced. Furthermore the provision of the restoring force calculating unit 20 and the cohesion force calculating unit 21 makes it possible to automatically calculate the restoring force of the apparatus itself including the movable support 8 and the movable container segment 5b for automatic correction of the measured values, consequently affording measurements with greatly improved accuracy.

When the container segments 5a, 5b and the weight 25 are formed with projections 26a, 26b and 26c respectively in such arrangement that the projections 26a, 26b on the segments 5a, 5b, when joined together, will oppose the projection 26c on the weight 25 as shown in FIG. 4, the compacted specimen S will be dividable along a predetermined plane more effectively. This assures measurement with enhanced precision.

The movable container 5b may be supported in suspension by quadrilateral rigid frames 27a, 27b shown in FIG. 5 and each having a downward knife edge 28a at its upper portion and an upward knife edge 28b at its upper portion, the downward knife edges 28a bearing on the posts 6a, 6b with the movable support 8 resting on the upward knife edges 28b. The arrangement in which the movable container segment 5b is supported by the rigid frames 27a, 27b serves to reduce the vertical movement of the container segments 5a, 5b relative to each other even when the specimen S is compacted with an increased force. This results in measurements with improved precision. The combination of the movable support 8 and the plate springs 7a, 7b or the frames 27a, 27b, or other arrangement will be referred to collectively as support means.

Figure 6:
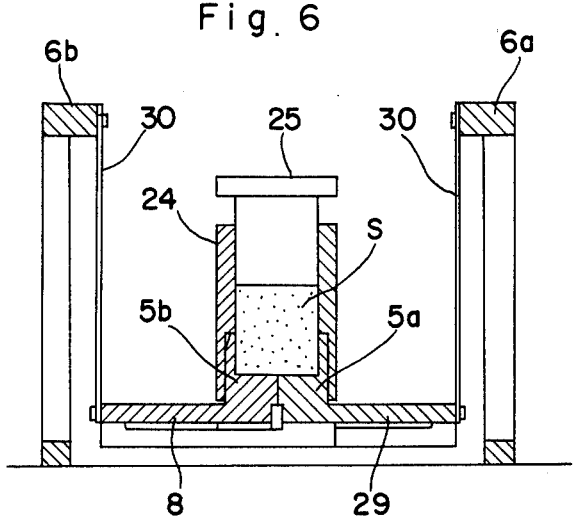
Figure 7:
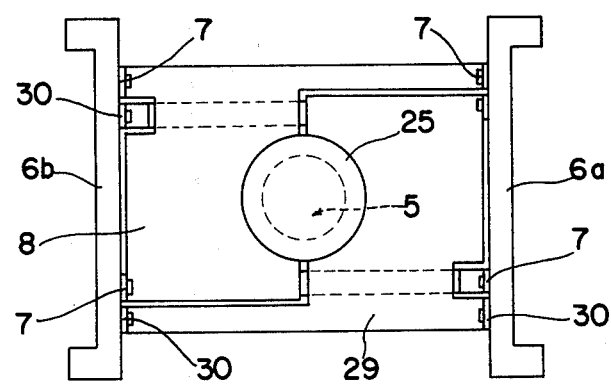
FIG. 7 is a plan view of the embodiment shown in FIG. 6.
Figure 8:
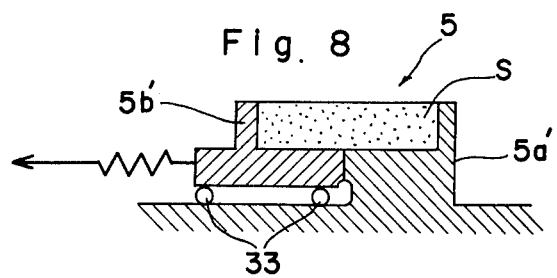
FIG. 8 is a fragmentary view in vertical section showing a conventional apparatus.

Further as seen in FIGS. 6 and 7, a support 29 for the fixed container segment 5a, like the movable support 8, may be supported in suspension by the posts 6a, 6b by means of support springs 30 resembling the plates springs 7 for the support 8 so as to eliminate the vertical movement of the container segments 5a, 5b relative to each other even when the specimen S is compacted with an increased force. This arrangement effectively prevents occurrence of a defect in the specimen S in respect of its strength when it is compacted, permitting measurement with greatly improved accuracy.

The means for moving the movable container segment 5b can be modified variously and will be referred to as drive means 15.

The means for measuring the external force to be applied to the movable container segment 5b by the drive means 15, as well as the means for measuring the distance of displacement of the movable container segment 5b, can also be modified variously. The former means will be referred to as an external force detecting unit 14, and the latter as a displacement detecting unit 19.

The construction of the calculation indicating device 23 can also be modified variously.

We claim:

1. An apparatus for measuring the cohesion force of a particulate material comprising,
    a bottomed container (5) composed of a fixed container segment (5a) and a movable container segment (5b) separable from each other for containing the particulate material (S) as compactly placed therein,
    drive means (15) for moving the movable container segment (5b) in a direction substantially perpendicular to the plane of separation of the container (5) to divide the particulate material (S) in the container (5) into two, and an external force detecting unit (14) for detecting the external force to be applied to the movable container segment (5b) by the drive means (15), the apparatus being characterized in that at least the movable container segment (5b) of the two container segments (5a), (5b) is suspended from and retained by swingable or deflectable support means.

2. An apparatus as defined in claim 1 characterized in that the support means comprises a movable support (8) and deflectable plate springs (7a), (7b).

3. An apparatus as defined in claim 2 characterized in that the fixed container segment (5a) is also retained in suspension by a support (29) resembling the movable support (8) and by support springs (30) resembling the plate springs (7a), (7b).

4. An apparatus as defined in any one of claims 1 to 3 further comprising,
 - a unit (19) for detecting the distance of displacement of the movable container segment (5b) from its spontaneously resting position, and
 - a unit (20) for calculating the restoring force of the movable container segment (5b) and the support means (8), (7a, 7b), (27a, 27b) based on the value detected by the displacement detecting unit (19).

5. An apparatus as defined in claim 4 further comprising, a unit (21) for calculating the cohesion force of the particulate material (S) by subtracting the value calculated by the restoring force calculating unit (20) from the value detected by the external force detecting unit (14).

6. An apparatus as defined in claim 1 characterized in that the support means comprises a movable support (S) and quadrilateral rigid frames (27a), (27b).

* * * * *